United States Patent [19]
Watanabe et al.

[11] Patent Number: 5,694,214
[45] Date of Patent: Dec. 2, 1997

[54] SURFACE INSPECTION METHOD AND APPARATUS

[75] Inventors: Tetsuya Watanabe; Yoshio Morishige, both of Honjo; Hisato Nakamura, Saitama-ken, all of Japan

[73] Assignee: Hitachi Electronics Engineering Co., Ltd., Tokyo, Japan

[21] Appl. No.: 768,553

[22] Filed: Dec. 18, 1996

[30] Foreign Application Priority Data

Jan. 8, 1996 [JP] Japan .................................. 8-018124

[51] Int. Cl.$^6$ .................................................. G01N 21/00
[52] U.S. Cl. ..................... 356/237; 356/247; 356/399; 356/124
[58] Field of Search .................................. 356/237, 247, 356/253, 252, 399, 124

[56] References Cited

U.S. PATENT DOCUMENTS

| | | | |
|---|---|---|---|
| 4,135,823 | 1/1979 | Hörvallius | 356/247 |
| 5,151,753 | 9/1992 | Whitman, III | 356/247 |
| 5,311,288 | 5/1994 | Shahar | 356/399 |

OTHER PUBLICATIONS

U.S. application No. 08/678,069, Jul. 10, 1996.
U.S. application No. 08/744,454, Nov. 07, 1996.

*Primary Examiner*—Frank G. Font
*Assistant Examiner*—Reginald A. Ratliff
*Attorney, Agent, or Firm*—Fay, Sharpe, Beall, Fagan, Minnich & McKee

[57] ABSTRACT

A surface inspection apparatus of the present invention comprises an optical sensor having a plurality of detecting portions arranged in a sub-scan direction, the detecting portions being responsive to the scattering light for producing the detection signals correspondingly to respective pixels, a detection optical system including an objective lens and disposed between the optical sensor and the thing to be inspected, a projection optical system for irradiating the thing to be inspected with the laser beam having a cross sectional area large enough to cover the scattering light to be received by the plurality of the detecting portions through the detection optical system and an inspection device responsive to the detection signals for inspecting the surface of the thing to be inspected, wherein one of the detection optical system lens and the optical sensor is mounted such that a setting axis thereof is aligned in a plane perpendicular to an optical axis of the detection optical system lens with a light receiving direction which makes an angle with respect to the sub scan direction and in which shading is minimum.

9 Claims, 5 Drawing Sheets

SURFACE INSPECTION METHOD AND APPARATUS

2. DESCRIPTION

2-1. Technical Field

The present invention relates to a surface inspection method and apparatus and, particularly, to a surface inspection method and apparatus of an X-Y scanning type which can reduce the effect of shading of an optical detection system and can detect extraneous substance or contaminants on a surface with an improved preciseness.

2-2. Background Art

As a surface inspection apparatus, a defect inspection apparatus and an extraneous substance or contaminants inspection apparatus are known for inspecting a defect and/or contaminants on a surface of a wafer, a mask, a disk substrate or a liquid crystal substrate, etc. The contaminants inspection apparatus is used to inspect contaminants or defects on a surface of a wafer, mask or liquid crystal substrate, particularly, on a patterned surface thereof. In this specification, the term "surface inspection" means an inspection of surface defect, surface flaw and/or contaminants adhered to a surface, which may produce problems.

Considering a wafer contaminants inspection apparatus as an example of the surface inspection apparatus, there are two types of wafer contaminants inspection apparatus, one being X-Y scan type in which a surface of a wafer is scanned with laser beams in X and Y directions and the other being rotary scan type in which a surface of wafer is scanned spirally or concentrically with a laser beam while the wafer is rotated.

Although the wafer contaminants inspection apparatus of the X-Y scan type has an advantage that it can detect a position at which a contaminant is detected more accurately than that of the rotary scan type, the inspection efficiency thereof is lower than that of the rotary type. In order to improve the inspection efficiency of the wafer contaminants inspection apparatus of the X-Y scan type, a contaminants inspection apparatus was proposed in which a laser beam is collimated to form a rectangular contaminant detection area on a wafer and a contaminant is detected by focusing an image of the contaminant detection area on a light receiving plane of a one dimensional optical sensor (for example, a CCD sensor) through a lens of a detection optical system and X-Y scanning the image. U.S. Ser. No. 08/678,069 based on the above mentioned technique, entitled "Extraneous Substance Inspection Method and Apparatus" and assigned to the same assignee of this application was filed on Jul. 10, 1996.

However, when a laser beam is collimated to form a rectangular contaminant detection area on a wafer and a contaminant is detected by focusing an image of the contaminant detection area on a light receiving plane of a one dimensional optical sensor through a lens of a detection optical system, a level of a detection signal from the optical sensor varies correspondingly to a light receiving position of the optical sensor due to an influence of shading of an objective lens or a focusing lens of the detection optical system and, therefore, it is impossible to detect contaminant with high precision.

For example, from a measurement of the influence of shading for a CCD 35 mm long including 5000 pixels, it has been found that a level of the detection signal from a pixel arranged in a periphery of a center pixel is about 50% of that from the center pixel.

The influence of shading of the detection optical system may occur in surface inspection apparatuses having similar constructions to that of the mentioned apparatus.

3. SUMMARY OF THE INVENTION

An object of the present invention is to provide a surface inspection apparatus capable of reducing shading due to lenses of a detection optical system thereof.

Another object of the present invention is to provide a contaminant inspection apparatus capable of reducing shading due to lenses of a contaminant detection optical system thereof and improving throughput of the inspection.

A further object of the present invention is to provide a surface inspection apparatus capable of reducing shading of a detection optical system thereof.

A still further object of the present invention is to provide a contaminant inspection apparatus capable of reducing shading of a contaminant detection optical system and improving the throughput of inspection.

In order to achieve the above objects, the surface inspection apparatus according to the present invention, in which a surface condition of a thing to be inspected is inspected on the basis of detection signals each corresponding to intensity of scattering light obtained by X-Y scanning the thing to be inspected with a laser beam making a predetermined angle with respect to a surface of the thing in one of X and Y direction as a main scan direction and the other as a sub-scan direction, is featured by comprising an optical sensor having a plurality of detecting portions arranged in the sub-scan direction, the detecting portions responsive to the scattering light for producing the detection signals correspondingly to respective pixels, a detection optical system including an objective lens and disposed between the optical sensor and the thing to be inspected, a projection optical system for irradiating the thing to be inspected with the laser beam having a cross sectional area large enough to cover the scattering light to be received by the plurality of the detecting portions through the detection optical system and an inspection device responsive to the detection signals for inspecting the surface of the thing to be inspected, wherein one of the detection optical system lens and the optical sensor is mounted such that a setting axis thereof is aligned in a plane perpendicular to an optical axis of the detection optical system lens with a light receiving direction which makes an angle with respect to the sub scan direction and in which shading is minimum.

In the present invention, the detection optical system lens or the optical sensor is mounted such that the setting axis thereof is aligned in the plane perpendicular to the optical axis of the detection optical system lens with the light receiving direction which makes an angle with respect to the sub scan direction and in which shading is minimum and the scattering light of the laser beam emitted from the light projection optical system is received by the detection portions of the optical sensor. Therefore, the effect of shading due to the lens of the detection optical system is reduced and thus the surface inspection apparatus can inspect a surface condition of the thing highly precisely.

In a case where the optical sensor is aligned to the light receiving direction in which the shading effect is minimum, the rectangular inspection area formed on the surface of the thing to be inspected by the laser beam is large enough to cover at least a light receiving area of the optical sensor, with a long side of the rectangular area being in parallel to the main scan direction, so that it becomes unnecessary to rotate the light projection optical system in concomitant with rotation of the optical sensor.

In the method of inspecting a surface condition, according to the present invention, the predetermined angle of the optical sensor or the detection optical system is determined as to be described later and, after the optical sensor of the detection optical system is rotated by the setting angle and mounted on the apparatus, the inspection is performed.

Now, a method of obtaining the setting angle will be described. The method utilizes a measuring device comprising a light source optical system for focusing an image of a point-source light in a focal point of a detection optical system having an objective lens, a light receiving unit, a measuring optical system including the objective lens detachably coupled thereto with an optical axis of the detection optical system is aligned with an optical axis of the detection optical system, for focusing the image of the point-source of light from the detection optical system in a light receiving surface of the light receiving unit, a first moving means for moving the measuring optical system along the optical axis of the measuring optical system, a second moving means for linearly moving the measuring optical system in a direction perpendicular to the optical axis of the measuring optical system and a mathematical operation processor for obtaining a level of the image of the point-source light obtained from the light receiving unit together with 2-dimensional coordinates of respective measuring points by 2-dimensionally moving the measuring optical system by the first and second moving means and for outputting data of levels of light from the respective measuring points, which are the same as the level of the image of the point-source light. The method comprises the map acquisition step of obtaining a map of the levels equal to the level of the image of the pint-source light and the angle acquisition step of obtaining an angle of the light receiving direction in which the shading effect of the lens of the detection optical system in the plane perpendicular to the optical axis of the measuring optical system is minimum from the map. The angle obtained in the angle acquisition step is the setting angle.

As mentioned, the measuring device operates to focus the image of the point-source light in the light receiving plane of the light receiving unit through the measuring optical system and to 2-dimensionally move the same system along the optical axis thereof and one setting axis perpendicular to the optical axis. The levels of receiving light obtained by the light receiving unit at respective measuring points while the measuring optical system are moved 2-dimensionally are mapped as, for example, contour map. Thus, it is possible to obtain a map indicative of an attenuation of light transmitted through the lens of the detection optical system in XZ plane or YZ plane along the optical axis (Z axis) of the lens of the detection optical system and one of X and Y setting axes. The map indicates curvature of the lens.

As a result, it is possible to obtain an appropriate setting angle of the lens of the detection optical system from the map as the setting angle with which the shading is minimum and, thus, it is possible to reduce the influence of shading of the lens of the detection optical system due to different detecting positions of the optical sensor by mounting the optical sensor or the lens of the detection optical system on the surface inspection apparatus with the optical sensor or the lens of the detection optical system being rotated by the setting angle obtained from the map with respect to the sub scan direction. As a result, it is possible to improve the inspection accuracy. Further, since it is possible to set the detection area having a relatively long width in the sub scan direction, it is possible to improve the throughput of the surface inspection by X-Y scanning without lowering the inspection accuracy.

4. BRIEF DESCRIPTION OF THE DRAWINGS

5. DETAILED DESCRIPTION OF THE PREFERRED EMBODIMENTS

Figure 1:
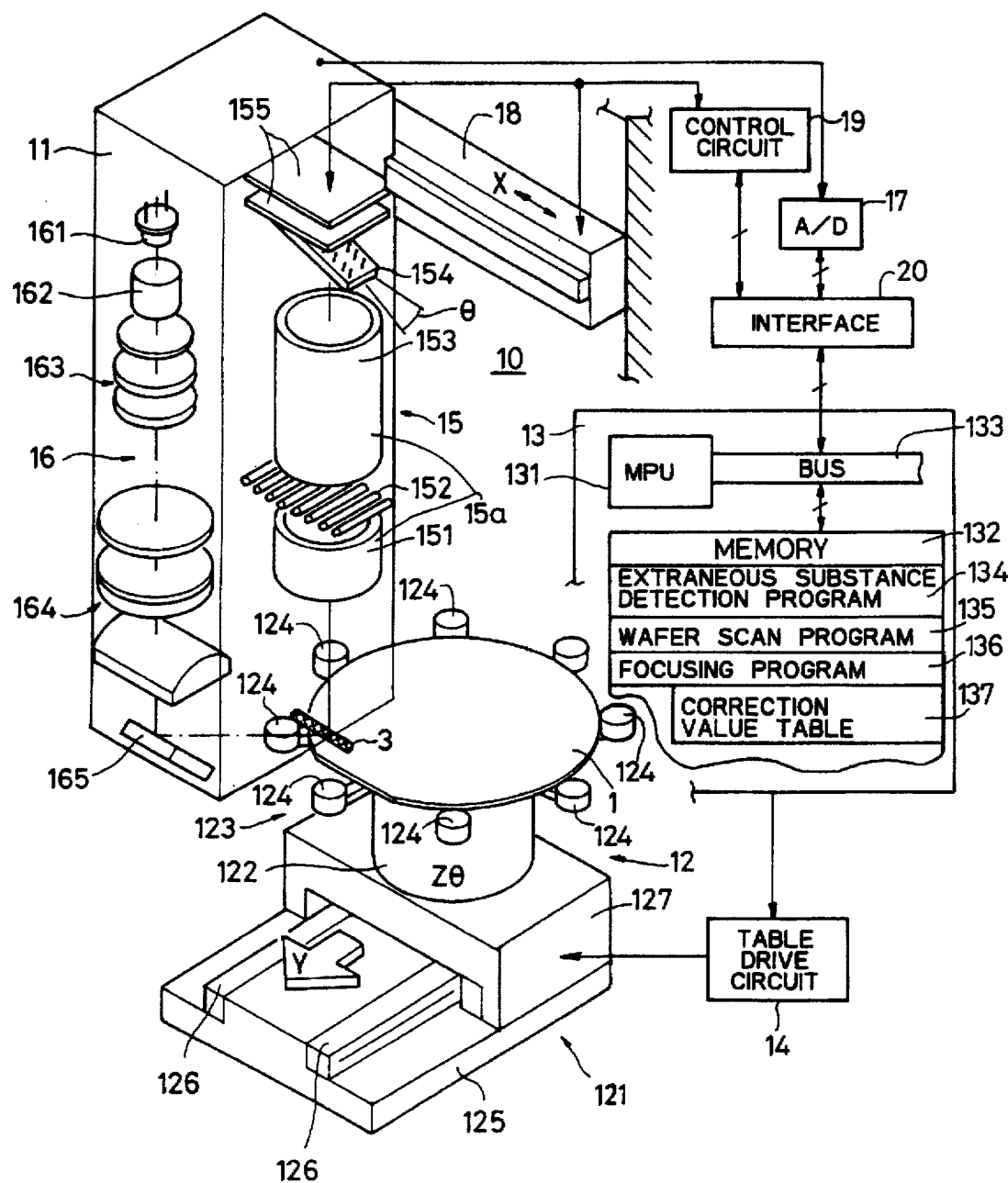
FIG. 1 is a schematic perspective view of a detection optical system of an embodiment of a wafer extraneous inspection apparatus to which a surface inspection apparatus of the present invention is applied, together with an electronic device associated therewith.

In FIG. 1, an extraneous substance inspection apparatus 10 comprises an extraneous substance inspection optical system 11, an inspection table 12 disposed below the extraneous substance inspection optical system 11, a data processing/control device 13, a table driving circuit 14, an A/D converter circuit(A/D) 17, an X moving mechanism 18, a control circuit 19 and an interface 20, a wafer 1 being mounted on the inspection table 12. The control circuit 19 responds to signals from the data processing/control device 13 through the interface 20 to produce various control signals for driving the X moving mechanism 18 and a CCD control/signal read circuit 155.

The extraneous substance inspection optical system 11 includes a detection optical system 15 and a light projection optical system 16 as shown and the light projection optical system 16 emits a laser beam having a predetermined width in a sub scan direction to an inspection area 3 (extraneous inspection area) on the wafer 1 and the detection optical system 15 disposed vertically above the wafer 1 receives upward scattering light therefrom. The extraneous substance inspection apparatus 11 is fixed to the X direction moving mechanism 18 and is shifted in an X direction. Incidentally, a length of the inspection area 3 in X direction is a width of 1 line in a main scan direction. Therefore, a moving pitch in the sub scan direction (X direction) corresponds to this width. Further, as will be described later, when a CCD sensor 154 is mounted with a setting angle θ with respect to the X setting axis direction (sub scan direction), the width of the inspection area 3 allows a light receiving area of the tilted CCD sensor 154 to be focused thereon (see a focus region 3a in FIG. 4).

The light projecting optical system 16 includes a semiconductor laser light source 161, condenser lens systems 162, 163 and 164 and a reflection mirror 165 and is adapted to collimate a laser beam into an ellipsoidal shape corresponding to the inspection area 3 and irradiate the inspection area 3 of the wafer 1 with the collimated laser beam at an angle of 30 degrees with respect to the surface of the wafer 1.

The detection optical system 15 includes an objective lens 151 facing to the inspection area 3 of the wafer 1, a spatial filter 152 disposed behind the objective lens 151, a condenser lens system 153 disposed behind the spatial filter 152, the previously mentioned CCD sensor 154 adapted to receive a whole image of the inspection area 3 focused by the condenser lens system 153 and a CCD control/signal read circuit 155 for reading a detection signal from the CCD sensor 154. The objective lens 151 and the condenser lens system 153 of the detection optical system 15 constitute a lens unit 15a of a telecentric system whose front focal point is set on the wafer 1 and a back focal point set on the light receiving surface of the CCD sensor 154.

The CCD control/signal read circuit 155 is controlled by the data processing/control unit 13 through the interface 20 and the control circuit 19 to serially read the detection signal detected correspondingly to intensity of light received, send it to the A/D 17 and send the detection signal digitized by the A/D 17 to the data processing/control device 13 through the interface 20 as a detection signal (digital value).

The detection optical system 15 is arranged such that the inspection area 3 is located at a position in Y direction corresponding to a head portion of the wafer 1 at a moment when the wafer 1 is started to move in the main scan direction (Y direction). Since the wafer 1 is circular in shape, a portion of the inspection area 3 can be placed outside the wafer 1. In order to show such situation easily understandably, the inspection area 3 is illustrated somewhat inner side in X direction and somewhat inner side of the actual head portion of the wafer 1.

The CCD sensor 154 is mounted at the angle θ with respect to X setting axis direction as mentioned previously. The tilting angle θ coincides with an optimum axis of the detection optical system 15 which is measured by a lens curvature measuring device 100 shown in FIG. 2 with using X setting axis as a reference. A center position of the CCD sensor 154 substantially corresponds to a position of a pixel which receives light having maximum level among others from the detection optical system 15.

The data processing/control unit 13 is usually constituted with a MPU 131 and a memory 132, etc., and stores the signal received from the A/D 17 through the interface 20 and a bus 133 in the memory 132. The memory 132 has stored various programs including an extraneous substance detection program 134, a wafer scan program 135 and a focusing program 136, etc. A correction value table 137 is further provided.

The table driving circuit 14 drives the inspection table 12 to reciprocally move in Y direction in response to an execution of the wafer scan program 135 by the MPU 131. Further, at the moment when the inspection table 12 is moved in Y direction by a distance corresponding to D+α (D is a diameter of the wafer 1 and α is a margin of scanning), the table driving circuit 14 rotates a Zθ table 142 by 180 degrees to return the table in Y direction by the distance corresponding to D+α. That is, this is a driving circuit for performing a reciprocal scan in Y direction.

In a process of execution of the extraneous substance detection program 134, the MPU 131 executes the wafer scan program 135 and the focusing program 136 by calling them. Further, the MPU 131 corrects the level of detection signal by referencing values in the correction value table 137 during the execution of the extraneous substance detection program 134 (the correction will be described later).

The inspection table 12 is constituted with a Y table 121, the Zθ table 122 and a center positioning mechanism 123 provided at the Zθ table 122. The center positioning mechanism 123 is a restriction mechanism including a plurality of rollers 124 arranged along the outer circumstance of the wafer 1. Since the plurality of rollers 124 are designed to permit an interlocked rotation from the outside to the inside like so called shutter diaphragm, the center of the wafer 1 carried on the inspection table 12 is positioned at the center of the inspection table 12.

The Y table 121 is constituted with a base plate 125, rails 126 provided on the base plate 125 and a table 127 which is designed slidable on the rails 126 in Y direction.

The Zθ table 122 is a table carried on the table 127 and movement of the Zθ table in Z direction is performed by an elevation mechanism provided inside the table 127 and secured thereto. The elevation mechanism primarily moves the wafer 1 in vertical direction for focusing and sets the vertical position of the wafer 1.

Figure 2:
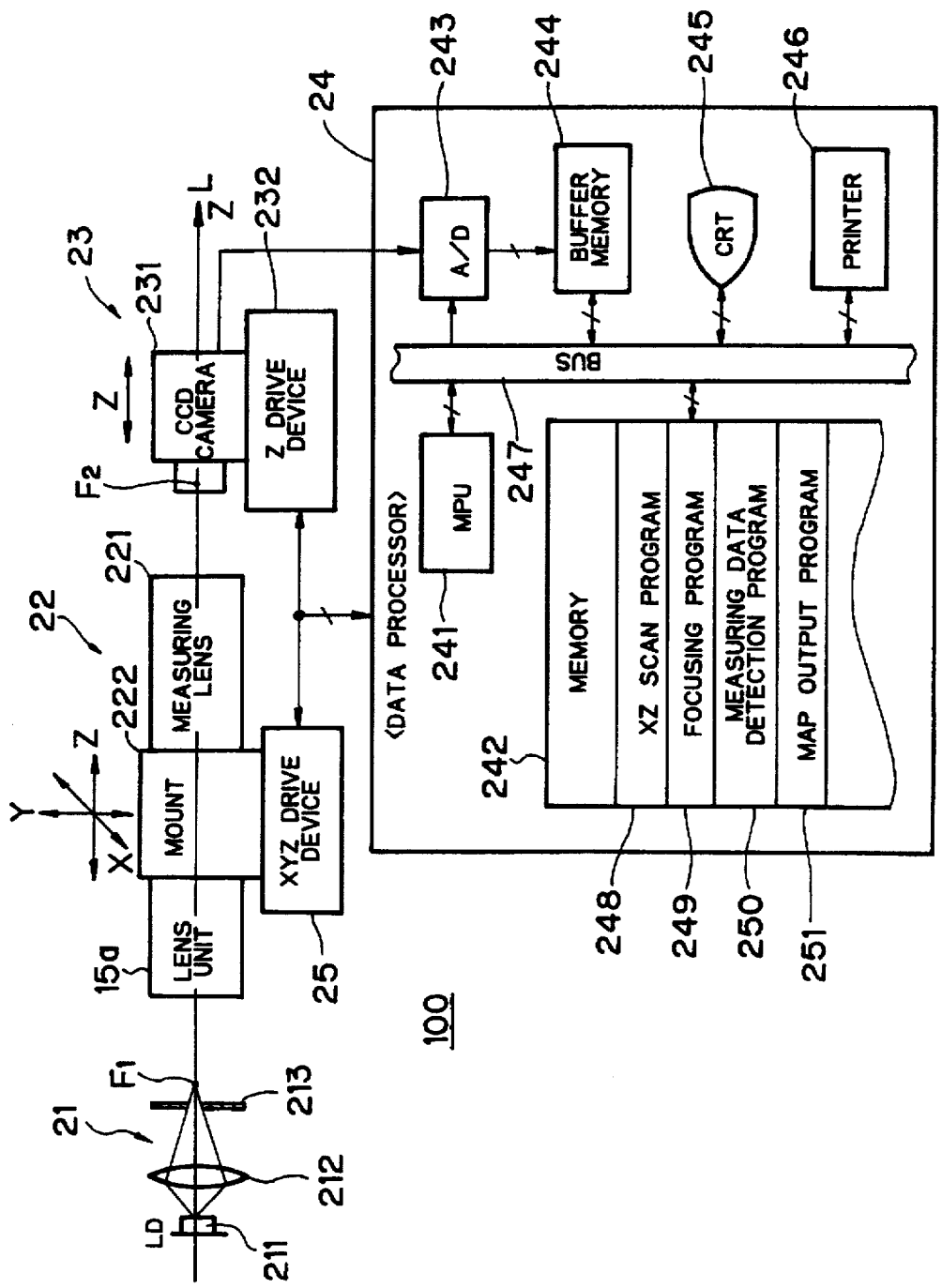
FIG. 2 shows a construction of a lens curvature measuring apparatus for measuring a curvature of lens.

The lens unit 15a of the detection optical system 15 shown in FIG. 2 is composed of the objective lens 151 and the focusing lens system 153, as mentioned previously. The lens unit 15a is to be measured by the lens curvature measuring device 100 shown in FIG. 2.

In FIG. 2, the lens curvature measuring device 100 includes a light source optical system 21, a measuring lens system 22, a camera system 23, a data processor 24 and a XYZ driving unit 25. A capital letter L in FIG. 2 indicates an optical axis which is common for the light source optical system 21, the measuring lens system 22 and optical lenses of the camera system 23 and coincides with Z axis of the XYZ coordinates system shown in FIG. 2.

The light source optical system 21 includes a laser light emitting diode (LD) 211, a focusing lens 212 for condensing laser light from the LD 211 and a pin-hole plate 213 and forms a point-light source in a focal point F1 on the optical axis L (Z axis).

The lens unit 15a is usually provided with an index or mark indicative of X or Y setting axis as a reference for mounting it on a mount 222 of the measuring lens system 22 in such a way that the front focal point thereof is positioned in the focal point F1. The measuring lens system 22 is composed of a measuring lens 221 and the lens mount 222. The mount 222 couples the measuring lens 221 to the lens unit 15a while maintaining a predetermined focusing relation between them with their optical axes being coincided. In the predetermined focusing relation, an image of the point light source focused in a back focal point of the lens unit 15a is focused in a front focal point of the measuring lens 221 so that the image is focused in a back focal point of the measuring lens 221.

Since the front and back focal lengths of the lens unit 15a and the measuring lens 221 are known, the lens unit 15a is mounted on the mount 222 such that its back focal point coincides with the front focal point of the measuring lens 221. With this mounting, the above mentioned predetermined focusing relation is established. Further, the position F1 of the point light source of the light source optical system 21 and a focal length of a CCD camera 231 are also known.

The lens mount 222 is fixed to a XYZ driving device 25.

The measuring lens system 22 is moved in X and Y setting axes directions and Z direction together with the lens unit 15a by moving the mount 222 by the XYZ driving device 25.

The measuring lens 221 is adapted to position the point source of light focused on its back focal point on the focal point F2 on the camera side and forms a lens system having a uniform and highly precise spherical surface with minimum spherical surface distortion. Therefore, an influence of spherical surface distortion on the measurement is substantially negligible. The camera system 23 includes the CCD camera 231 and a Z drive device 232 on which the CCD camera 231 is mounted. The Z driving device 232 is adapted to position a CCD focusing plane (light receiving device) of the CCD camera 231 in the focal point F2 of the measuring lens system 22 by moving the CCD camera 231 back and forth on the Z axis (optical axis L). The movement of the CCD camera 231 in Z direction is performed according to a control signal from the data processing device 24.

The data processing device 24 is constructed with a MPU (micro processor) 241, a memory 242, an A/D converter (A/D) 243 for converting an analog value into a 8-bit, 256-tone digital value, a buffer memory 244, a CRT display (CRT) 245 and a printer 246, etc. These circuits and devices are mutually connected to the MPU 241 through a bus 247 to exchange data with the MPU 241 and are controlled by the MPU 241.

Incidentally, an interface for interfacing between the bus 247, the XYZ driving device 25 and the Z driving device 232 is omitted in the figure for simplicity of illustration. Further, the XYZ driving device 25 and the Z driving device 232 include moving mechanisms (not shown) and driving control circuits (not shown) for driving the moving mechanisms according to signals from the MPU 241, respectively.

The memory 242 stores an XZ scan program 248 for XZ scanning by controlling the XYZ driving device 25, a focusing program 249 for focusing by controlling the XYZ driving device 25 and the Z driving device 232, a measuring data collecting program 250 and a map output program 251.

The MPU 241 executes the XZ scan program 248 to move the mount 222 in X direction and the measuring lens system 22 back and forth in Z direction by driving the XYZ driving device 25. Thus, the lens unit 15a for focusing the light from the point light source of the light source optical system 21 is scanned in X and Z directions with the light.

The MPU 241 executes the focusing program 249 to make the focal point of the lens unit 15a coincident with the focal point F1 by driving the XYZ driving device 25 in Z direction and align the center of the measuring lens system with the Z axis which is the optical axis L by driving it in X and Y directions. At this time, the position of the lens unit 15a becomes an original point (X=0, Y=0) in X and Y directions in XZ scanning or YZ scanning. Further, the MPU 241 makes the focusing plane of the CCD camera 231 coincident with the focal point F2 by driving the Z driving device 232. At this time, the position of the lens unit 15a becomes an original point (Z=0) in the scanning in Z direction.

The MPU 241 executes the measuring data collecting program 250 to actuate the A/D 243, which receives an image output of the CCD camera 231, when the spot (point light source image) is focused on the focusing plane of the CCD camera 231 to store the image output corresponding to 1 frame in the buffer memory 244 by A/D converting the image output according to a predetermined clock. And, the MPU 241 reads out the image data corresponding to 1 frame stored in the buffer memory 244 from the buffer memory 244, extracts a measuring data portion in a position corresponding to a position at which the light of the point light source is received and stores peak values of the measuring data portion extracted in the memory 242 together with the XZ coordinates (coordinates value of the lens unit 15a from the above mentioned original point) of the measuring point. Incidentally, the XZ coordinates is obtained from a relation between the control value given by the data processing device 24 to the XYZ driving device 25 for movement and the original point of the lens unit 15a.

Figure 4:
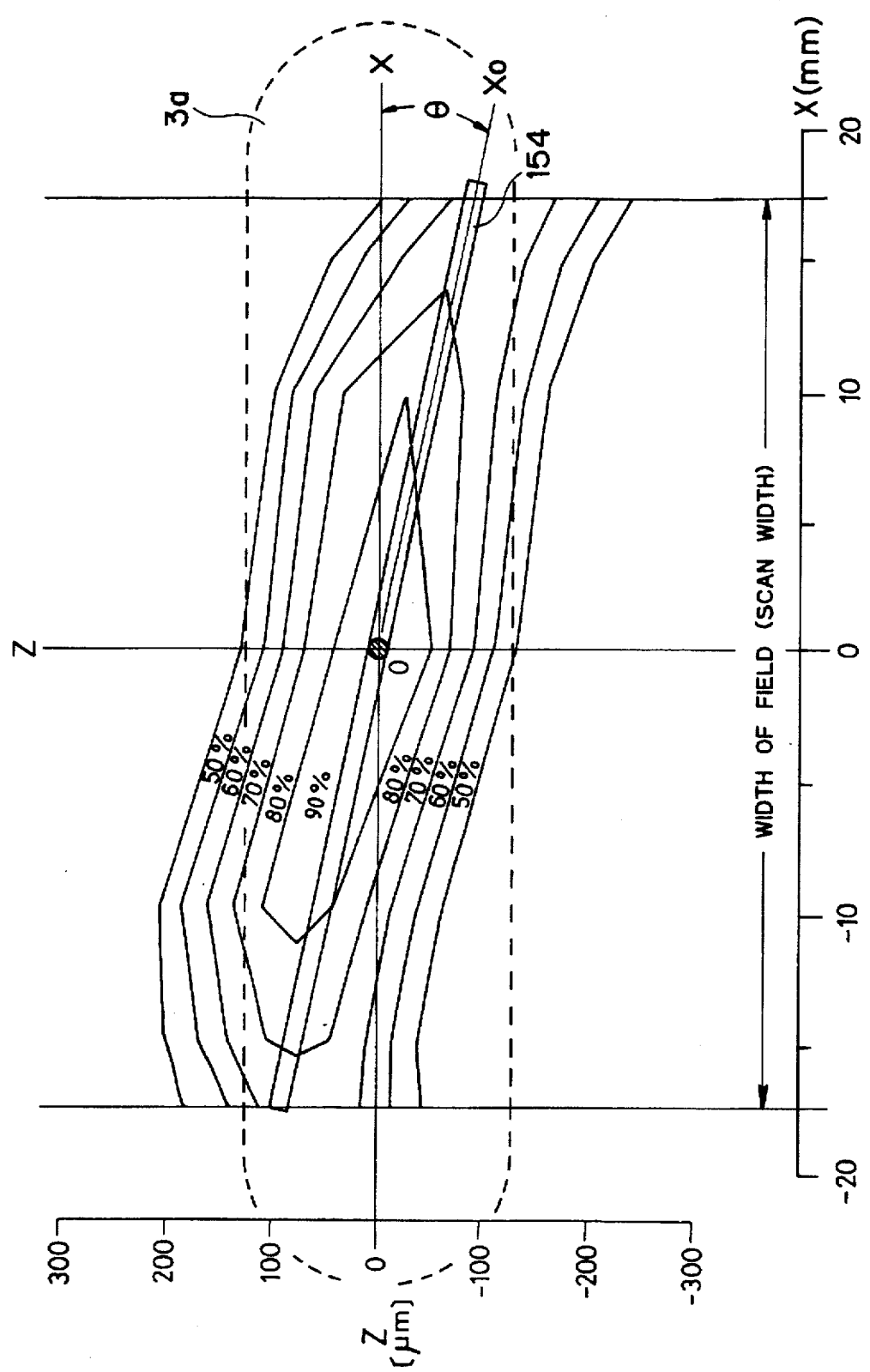
FIG. 4 shows a result of measurement of a lens curvature.

The MPU 241 executes the map output program 251 to detect data having maximum value from the data at the respective measuring points as the maximum receiving light level and its position. The XZ coordinates of the maximum receiving light level is read out and made the position as a center O (see FIG. 4). Further, percentage (%) of the respective measuring data with the maximum receiving light level being 100% are calculated correspondingly to the respective XZ coordinates (XZ scan positions). Further, contour map data is produced by converting the XZ coordinates into a coordinates having the center O as an original point and connecting the measuring data every 10%. Further, the MPU 241 extends this data to a display data to display it on the CRT display 245 or to supply it to the printer 246. FIG. 4 shows an example of data displayed.

Figure 3:
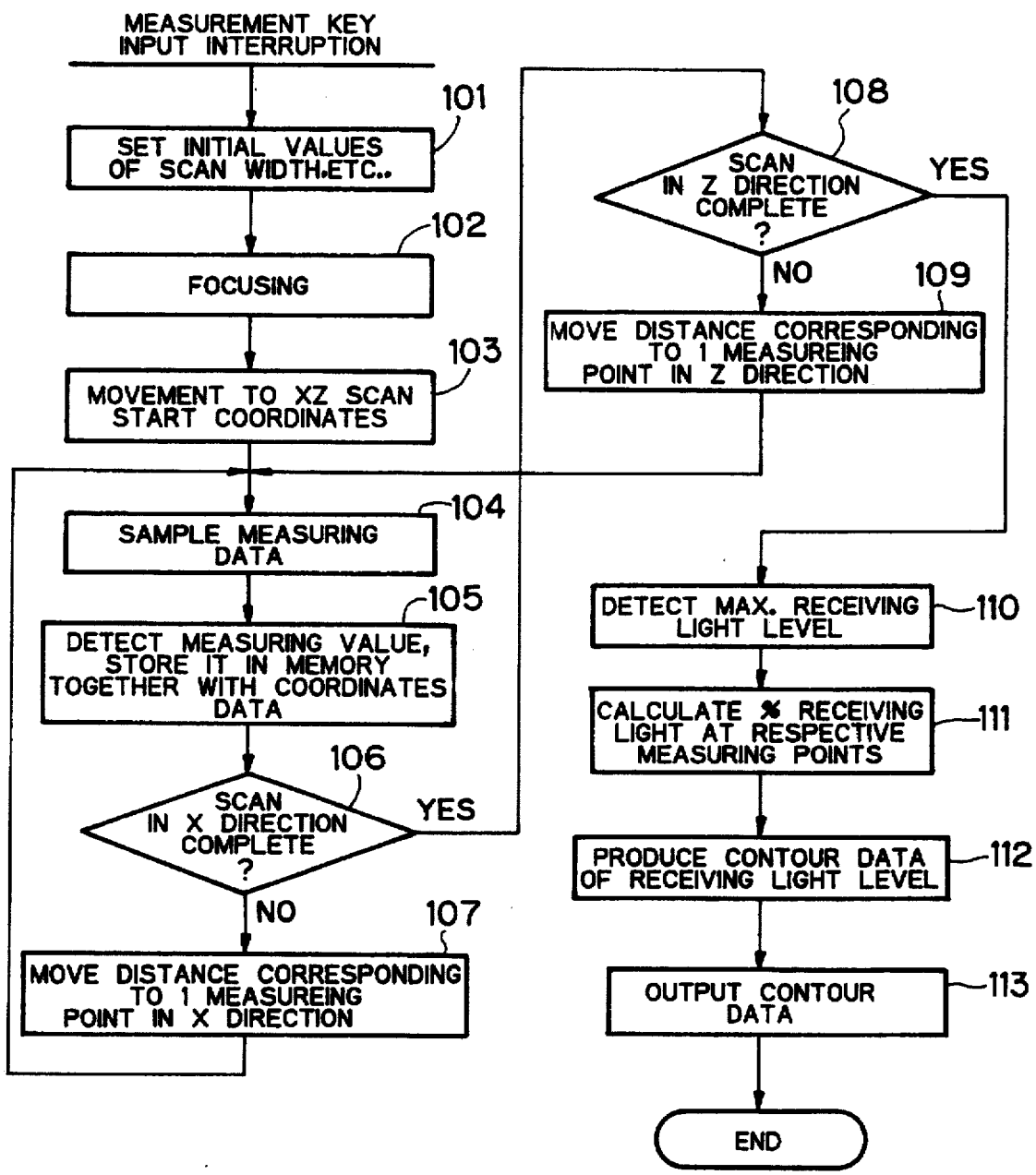
FIG. 3 is a flowchart of a measuring process of a lens curvature.

Now, a measurement processing to be performed by the data processor 24 for obtaining the measuring data of the curvature of lens shown in FIG. 4 will be described with reference to FIG. 3.

First, the measurement processing is started by a measuring key input interruption and initial values of scan width, etc., are set (step 101). With this, data such as scan widths in X and Z directions are input. As the initial values, the front and back focal points of the lens unit 15a and the measuring lens 221, the position F1 of the image of the point light source of the light source optical system 21 and the focal length of the CCD camera 231, etc., which are known are input.

The MPU 241 executes the focusing program 249 to make the front focal point of the lens unit 15a coincident with the focal point F1. Further, the MPU 241 aligns the center of the lens of the measuring lens system 22 with the optical axis L to make the focal plane of the CCD camera 231 coincident with the focal point F2 (step 102).

Then, the MPU 241 executes the XZ scan program 248 to position the measuring lens system 22 in the scan start point in XZ directions (step 103). For example, this start point may correspond to a position at a left lower corner in FIG. 4. This is determined by data input in the initial value setting step. In this example, the scan start point is set at a position X=−18 mm from the original point O of the scan area in X direction and 300 μm from the original point O of the scan area in Z direction. The positioning of the measuring lens system 22 (mount 222) is performed by moving the measuring lens system 22 toward the side of the focal point F1 in X direction and to a position Z=−300 μm in Z direction, in which position, the point light source image at the focal point F1 is projected onto the focal plane of the CCD camera 231 and a video signal thereof is supplied to the A/D 243.

Then, the MPU 241 executes the measurement data collecting program 25 to A/D convert the video signal at the start point (initial measuring point) by the A/D 243 and store data of the A/D converted receiving light level corresponding to 1 frame in the buffer memory 244 (step 104). Thus, the measuring data for 1 frame is collected. The MPU 241 obtains peak values of data among data stored in the buffer memory 244 which have levels not lower than a predetermined level as the measuring data and stores them in a predetermined area of the memory 242 together with the XZ coordinates of the measuring points thereof (step 105).

Then, the MPU 241 executes the XZ scan program 248 to determine whether or not the scan in X direction completes (step 106). When the scan is not completed, the measuring lens system 22 is moved to a next measuring point in X direction (step 107) and the process is returned to the step 104. This measurement is repeated similarly.

When the scan in X direction completes, it is determined whether or not the scan in Z direction completes (step 108). When the scan in Z direction is not completed, the measuring lens system 22 is moved by 1 measuring point in Z direction (step 109) and the process is returned to the step 104 to perform the scan in X direction again. The MPU 241 determines in the step 106 whether or not the scan in X direction is completed in the similar manner to the above mentioned.

The XZ scanning using the point light source is performed for the lens unit 15a as mentioned above. When it is determined in the step 108 that the scan in Z direction completes, the maximum receiving light level is detected.

The MPU 241 executes the map output program 251 to detect data having maximum value from the data stored in the memory 242 (step 110) and a position of its XZ coordinates is made the center O. With the maximum receiving light level being 100%, a coordinates data is produced by converting the sampled XZ coordinates using the position of the maximum receiving light level as the original point O and percentage (%) of the respective measuring data is calculated correspondingly to the respective XZ coordinates positions (step 111) and contour map data is produced by connecting the measuring data every 10% (step 112). Further, the MPU 241 displays this map data on the CRT display 245 and supplies it to the printer 246 (step 113).

FIG. 4 shows an example of map output in this manner. In the example shown in FIG. 4, the coordinates of the original point of the XZ scan and the coordinates of the original point O of the maximum receiving light level are coincident. Example in a case where the coordinates of these original points are not coincident is not shown since its illustration is very complex even if the difference is minute. Therefore, in FIG. 4, the maximum level is in the scan position X=0, Z=0 which position is the position of the original point O.

Incidentally, in a lens system formed symmetrically and having uniform curvature, a distribution of contour map to be obtained as a map shown in FIG. 4 might be ellipsoidal contour which is symmetrical about Z axis and about X axis. Therefore, a position of axis providing such contour or an axis which is near the axis and appropriate for receiving light is determined from this map. The axis is axis $X_0$. An angle between the axes X and $X_0$ is $\theta$ and this becomes the mounting angle. Further, the difference in coordinates between the original point of the XZ scan and the original point O as the maximum receiving light level becomes the amount of movement of the center of the CCD sensor 154. By this movement, it is possible to make the center of the CCD sensor 154 coincident with the original point O as the maximum receiving light level.

In FIG. 4, 154 indicates the arrangement of pixels of the CCD sensor 154. Further, the portion 3a encircled by a dotted line is the extraneous substance inspection area 3 focused on the CCD sensor 154. Further, in a case where there is some curvature of the measuring lens system 22 and its distortion is known, the MPU 241 may output the above mentioned map after the measuring data is corrected for the distortion due to the curvature.

The center position O and the mounting angle $\theta$ are obtained according to the map shown in FIG. 4. The center position of one of the detection optical system 15 and the CCD sensor 154 is moved by a distance corresponding to the difference in coordinates between the original pint O of the maximum receiving light level and the original point of the XZ scan and the CCD sensor 154 or the detection optical system is mounted on the extraneous substance inspection apparatus 10 by rotating the CCD sensor 154 or the detection optical system by $\theta$. Thus, the lens unit 15a of the detection optical system 15 and the CCD sensor 154 become the positional relation shown in FIG. 4. In this case, since the mounting position of the lens unit 15a in X, Y and Z directions is usually fixed, it is impossible to finely regulate it later. Therefore, it is preferable to tilt the CCD sensor 154 and then fixed. The CCD sensor 154 shown in FIG. 1 is an example of this case. At this time, the pixel in the center of the CCD sensor 154 is made coincident with the original point O at which the receiving light level becomes maximum. As a matter of course, when the lens unit 15a is mounted on the extraneous substance inspection apparatus, the position of the CCD sensor 154 is in the back focal point of the lens unit 15a.

The mounting of the CCD sensor 154 on the extraneous substance inspection apparatus may be performed by using screws or adhesive. It is preferable to provide a mechanism for finely regulating an angle and a center position in a position of the extraneous substance inspection apparatus in which the sensor 154 is to be mounted.

The measurement of the center position and the mounting angle of the CCD sensor in the XZ scanning was described. Alternatively, similar data can be obtained by changing the X axis to the Y axis by rotating the measuring lens system 22 by 90 degrees.

Particularly, when the measurements of the XZ scan and the YZ scan are performed, an average value $\theta m$ $(=(\theta x+\theta y)/2)$ of rotation angles in the X and Y setting axes is used as the rotation setting angle $\theta$ and the X setting axis (axis of the sub scan direction) is rotated by em in the X-Y plane of the mounting position, where $\theta x$ is a setting angle measured in XZ scan and $\theta y$ is a setting angle measured in YZ scan.

When this lens system is actually mounted on the measuring optical system, the axis on the optical sensor side is rotated by $\theta$ according to the data obtained in this manner so as to align it with an axis Xo. When the center position is deviated, it is possible to project an image having minimum shading on the optical sensor by rotating the optical sensor side axis by $\theta$ with respect to the mounting position and shifting it in X and Y directions such that the position O in which the receiving light level is maximum is coincident with the center of the receiving light.

Figure 5:
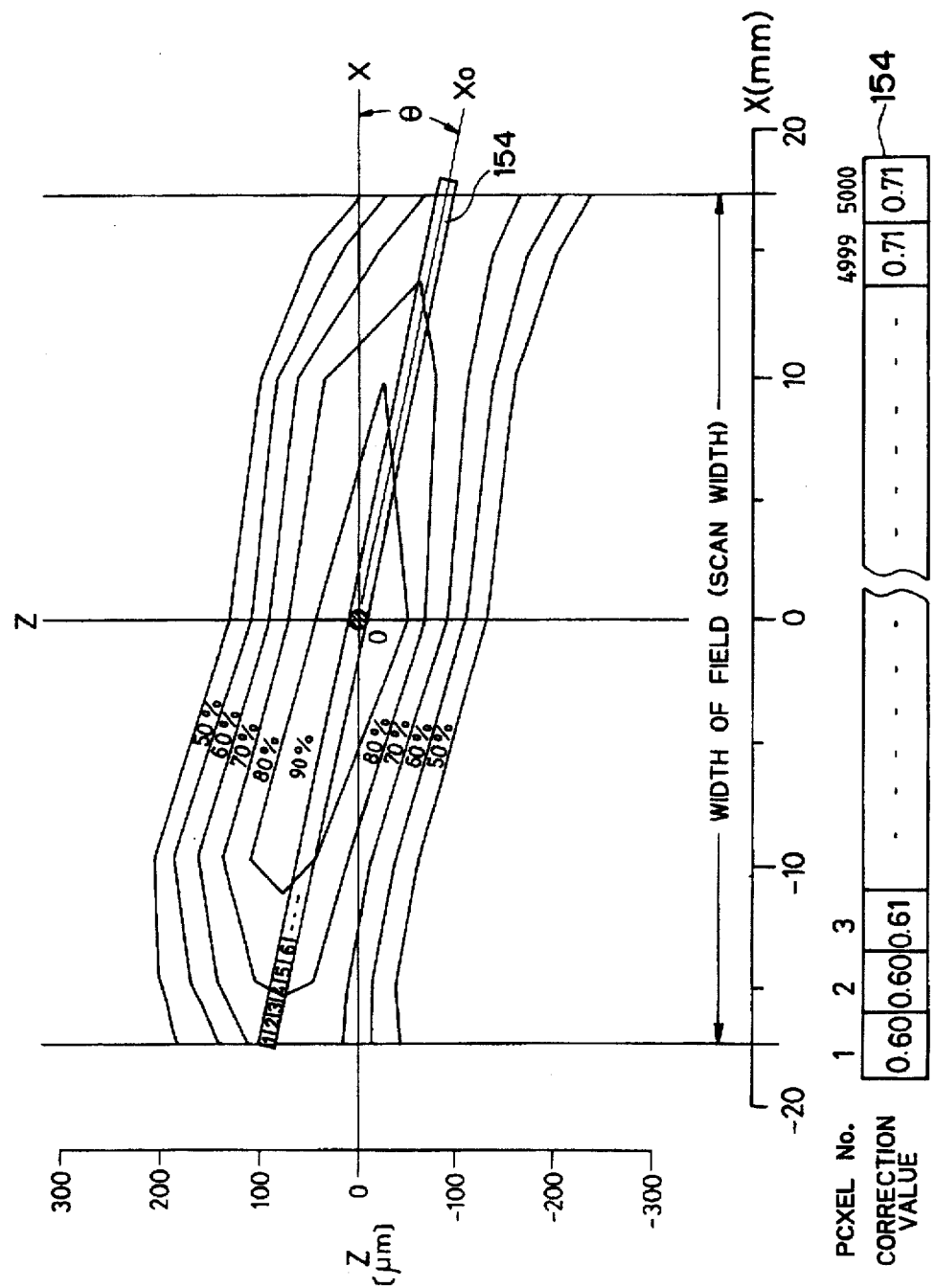
FIG. 5 is a relation between data stored in a correction value table and pixels of one line sensor.

FIG. 5 shows a relation between data stored in the correction value table 137 and pixels of a 1-line sensor.

In FIG. 5, numerals indicated above pixels of the CCD sensor 154 are pixel numbers of light receiving elements.

Correspondingly to the pixel numbers, receiving light level of the respective pixels of the CCD sensor 154 inclined by $\theta$ are indicated. For example, when a receiving light level of a certain pixel is 90%, ratio 0.90 is indicated for that pixel. These numerical values are input to the correction value table 137 of the memory 132 correspondingly to the respective pixel numbers.

The MPU 131 of the data processing/control unit executes the extraneous substance detection program 134 and obtains a level of a detection signal obtained by dividing a detection signal of a light receiving element corresponding to a certain pixel number from the A/D 17 in FIG. 1 by a ratio corresponding to the number of the pixel as a detection signal value of the light receiving element. With using it, the level of the detection signal is corrected.

Although, in this embodiment, the focusing is performed by moving the CCD camera along its axis in the Z direction, the focusing may be performed by moving the measuring lens system, the objective lens and the light source optical system, etc., together in Z direction while fixing the CCD camera. Further, the light receiving unit on the detection side is not limited to the CCD camera.

On the other hand, since the mounting state of the detection optical system is predetermined, a high precision rotary mechanism is necessary in order to rotate the detection optical system. According to the embodiment, a simple and high precision measurement can be done by employing the wide irradiation area 3 of the light projecting optical system provided by rotating the CCD sensor side by the angle $\theta$.

When defects or extraneous substance is detected by comparing detection signals corresponding to pixels, it is enough to delay a detection signal by a time corresponding to a positional shift corresponding to the tilting of the optical sensor by a delay circuit. A U.S. patent application based on such technique entitled "Extraneous Substance Inspection Apparatus for Patterned Wafer" and assigned to the same assignee as that of the present application was filed on Nov. 7, 1996.

Although the present invention has been described as applied to the extraneous substance inspection apparatus, the present invention can be applied to other inspection apparatuses for inspecting various surface conditions of such as magnetic disk, optical disk, mask substrate, LCD substrate, etc.

What is claimed is:

1. A surface inspection apparatus in which a surface condition of a thing to be inspected is inspected on the basis of detection signals each corresponding to intensity of scattering light obtained by X-Y scanning the thing to be inspected with a laser beam making a predetermined angle with respect to a surface of the thing in one of X and Y direction as a main scan direction and the other as a sub-scan direction, said surface inspection apparatus comprising:

an optical sensor having a plurality of detecting portions arranged in the sub-scan direction, said detecting portions being responsive to the scattering light for producing the detection signals correspondingly to respective pixels;

a detection optical system including an objective lens and disposed between said optical sensor and the thing to be inspected;

a projection optical system for irradiating the thing to be inspected with the laser beam having a cross sectional area large enough to cover the scattering light to be received by the plurality of said detecting portions through said detection optical system; and an inspection device responsive to the detection signals for inspecting the surface of the thing to be inspected, wherein one of said detection optical system lens and said optical sensor is mounted such that a setting axis thereof is aligned in a plane perpendicular to an optical axis of said detection optical system lens with a light receiving direction which makes an angle with respect to the sub scan direction and in which shading is minimum.

2. A surface inspection apparatus as claimed in claim 1, wherein said optical sensor is rotated by the predetermined angle and mounted, a width of the irradiating laser beam in the main scan direction is set in at least an area in which said optical sensor can receive light by the rotation thereof by the predetermined angle.

3. A surface inspection apparatus as claimed in claim 2, wherein said optical sensor comprises a line sensor and the predetermined angle is determined according to data of attenuation of a transmission light amount of said detection optical system lens measured by two dimensional scan along the optical axis of said detection optical system lens and one of X and Y setting axes.

4. A surface inspection apparatus as claimed in claim 3, wherein the attenuation is displayed as a contour map corresponding to the two dimensional scan and the predetermined angle is an angle between a direction corresponding to a major axis of an ellipse of said map and the one setting axis.

5. A surface inspection apparatus as claimed in claim 4, wherein said line sensor comprises a CCD sensor and said detection optical system lens comprises a telecentric lens unit including telecentrically arranged objective lens and having a front focal point set in a focusing position of said wafer and a back focal point coincident with a light receiving plane of said CCD sensor.

6. A surface inspection apparatus as claimed in claim 5, wherein the thing to be inspected is a wafer, the inspection of surface condition is to detect extraneous substance on a surface of said wafer, said map is obtained by a measuring device comprising a light source optical system for focusing an image of a point-source light in a focal point of said detection optical system lens unit, a light receiving unit, a measuring optical system including said detection optical system lens unit detachably coupled thereto with an optical axis of the measuring optical system is aligned with an optical axis of said detection optical system lens unit, for focusing the image of the point-source of light from said detection optical system lens unit in a light receiving surface of said light receiving unit, a first moving means for moving the measuring optical system along said optical axis of said measuring optical system, a second moving means for linearly moving said measuring optical system in a direction perpendicular to the optical axis of said measuring optical system and a mathematical operation processor for obtaining a level of the image of said point-source light obtained from said light receiving unit together with 2-dimensional coordinates of respective measuring points by 2-dimensionally moving said measuring optical system by said first and second moving means and for outputting data of levels of light from the respective measuring points, which are the same as the level of the image of said point-source light.

7. A surface inspection apparatus as claimed in claim 6, wherein the image of said point-source of light is formed by a pin-hole and said light receiving unit comprises a CCD camera.

8. A method of inspecting a surface of a thing, in which a surface condition of a thing to be inspected is inspected on the basis of detection signals from an optical sensor having a plurality of detecting portions arranged in the sub-scan direction, each of said detection signals corresponding to intensity of scattering light obtained by X-Y scanning the thing to be inspected with a laser beam making a predetermined angle with respect to a surface of the thing in one of X and Y direction as a main scan direction and the other as a sub-scan direction, said surface inspection method comprising:

a map acquisition step of obtaining a map of levels equal to a level of the image of the point-source light by using a measuring device comprising a light source optical system for focusing an image of a point-source light in a focal point of a detection optical system lens unit, a light receiving unit, a measuring optical system including said detection optical system lens unit detachably coupled thereto with an optical axis of the measuring optical system is aligned with an optical axis of said detection optical system lens unit, for focusing the image of the point-source of light from said detection optical system lens unit in a light receiving surface of said light receiving unit, a first moving means for moving the measuring optical system along said optical axis of said measuring optical system, a second moving means for linearly moving said measuring optical system in a direction perpendicular to the optical axis of said measuring optical system and a mathematical operation processor for obtaining a level of the image of said point-source light obtained from said light receiving unit together with 2-dimensional coordinates of respective measuring points by 2-dimensionally moving said measuring optical system by said first and second moving means and for outputting data of levels of light from the respective measuring points, which are the same as the level of the image of said point-source light;

an angle acquisition step of obtaining an angle of the light receiving direction in which the shading effect of the lens of the detection optical system in the plane perpendicular to the optical axis of the measuring optical system is minimum from the map; and a step of making a relation between the detection optical system lens and the optical sensor a state where they are rotated by a setting angle in a light receiving direction in which shading is minimum, wherein the surface condition is inspected on the basis of the level of the detection signal.

9. A method as claimed in claim 8, wherein the image of the point-source of light is formed by a pin hole, the detection optical system lens is a telecentric lens unit, the light receiving unit is a CCD camera, the mathematical operation processor includes a micro processor and a memory and is adapted to receive a signal obtained by A/D converting the detection signal from the optical sensor and obtain the light receiving levels of the respective measuring points and the map displays the attenuation of transmission light amount of the detection optical system lens as contour lines.

* * * * *